United States Patent
Callahan

(10) Patent No.: US 6,438,238 B1
(45) Date of Patent: Aug. 20, 2002

(54) STETHOSCOPE

(76) Inventor: Thomas F. Callahan, P.O. Box 1579, Grantham, NH (US) 03753

( * ) Notice: Subject to any disclaimer, the term of this patent is extended or adjusted under 35 U.S.C. 154(b) by 0 days.

(21) Appl. No.: 09/616,244

(22) Filed: Jul. 14, 2000

(51) Int. Cl.$^7$ ................................................ A61B 7/04
(52) U.S. Cl. ........................ 381/67; 181/131; 600/528; D24/134
(58) Field of Search ................... 381/67, 160; 181/131, 181/137, 155, 156, 158; 600/528, 586; D24/134

(56) References Cited

U.S. PATENT DOCUMENTS

| | | | |
|---|---|---|---|
| 3,076,870 A | | 2/1963 | Jones, Jr. ........................ 179/1 |
| 3,130,275 A | | 4/1964 | Hagey .......................... 179/110 |
| 3,881,056 A | * | 4/1975 | Gibson et al. ................ 381/160 |
| 3,895,188 A | | 7/1975 | Ingraham .................. 179/1 MF |
| 4,149,034 A | * | 4/1979 | Kendall ........................ 381/160 |
| 4,550,609 A | * | 11/1985 | Johnson ....................... 181/176 |
| 4,995,473 A | | 2/1991 | Packard ........................ 181/137 |
| 5,532,438 A | * | 7/1996 | Brown .......................... 181/155 |
| 5,578,799 A | | 11/1996 | Callahan et al. ............. 181/137 |
| 5,853,005 A | * | 12/1998 | Scanlon ........................ 381/166 |
| 5,920,038 A | * | 7/1999 | Foster .......................... 181/131 |
| 5,931,792 A | * | 8/1999 | Packard et al. ............. 600/528 |

FOREIGN PATENT DOCUMENTS

JP 6-181921 * 7/1994 ................... 381/67

OTHER PUBLICATIONS

The Big Brother Game, Scott French, Carol Publishing Group, New York, 1990, pp. 13–14.

* cited by examiner

*Primary Examiner*—Xu Mei
(74) *Attorney, Agent, or Firm*—Michael J. Weins; Jeffrey E. Semprebon

(57) ABSTRACT

A chest piece for a stethoscope has a housing with a cavity. The cavity has a cavity surface which is paraboloid in shape, having an apex, an axis, and a focal point. The cavity terminates at the apex and an opening, and the focal point resides in the cavity. A transducer is positioned at the focal point. The parabolic shape of the cavity surface acts to reflect sound waves transmitted normal to the opening to the transducer, while reflecting other sound waves. A mechanical wave guide with a series of parallel passages preferably extends across the opening. Preferably, a membrane with a convex surface covers the opening. The cavity is preferably filled with a liquid or gel having physical characteristics similar to human flesh. To reduce noise from motion of the chest piece across the skin, the stethoscope can be activated by a pressure switch responsive to fluid pressure inside the cavity.

27 Claims, 7 Drawing Sheets

STETHOSCOPE

FIELD OF THE INVENTION

The present invention relates to a stethoscope, more broadly sometimes referred to as a vital signs monitor, and more particularly to a stethoscope which has improved fidelity of reproduced body-generated signals.

BACKGROUND OF THE INVENTION

For the purpose of this application, a stethoscope is defined as a device having a body signal transducing device which is placable on the body, coupling to the skin and serving as the pick-up for sounds generated in the body and transmitted through the flesh which, for the purpose of this application, is defined as the skin and underlying tissue. Since the stethoscope is frequently used to monitor sounds due to action of the heart, in which case the body signal transducing device is placed on the chest, the body signal transducing device is frequently referred to a chest piece, and is hereinafter referred to as such. The stethoscope as used in this application is considered in its broadest sense. The stethoscope, as it is defined in the present application, also has an output element which allows a user of the stethoscope to perceive the sounds being generated by the body. This output element can be provided by a variety of devices such as earphones, speakers, recording mediums (capable of being played back), visual monitors, etc., all hereinafter referred to as earphones. In the stethoscope, the chest piece and the earphones are operatively connected by a transmission medium which, for a classical mechanical stethoscope where the output of the chest piece is transmitted through a gaseous medium such as air, can be a tube containing a column of air. Alternatively, for an electronic stethoscope where the output of the chest piece is an electronic signal, the transmission medium can be composed of a variety of electronic components.

There are a variety of stethoscopes which have been developed. All of these are based on techniques for sensing the sound emitted from the body by monitoring the sound that radiates from the body and is transmitted through a confined volume of a fluid. Historically, the fluid employed in the stethoscopes was air, and attempts were made to mechanically amplify the sounds generated by the body. Sound, being a wave form of energy, is classically described in terms of its intensity, reported in decibels (dB) with larger values corresponding to greater intensity, and its frequency, reported in cycles per second or Hertz (Hz).

The stethoscope was invented by Rene Laennec in France in 1819. His stethoscope was a monaural device which was fashioned from wood and had an input opening and an associated sound chamber or so-called "sound accumulator", which was modeled on the shape of a musical horn. A sound transmission conduit (also fabricated from wood) was a straight, smooth bore which coupled the sound chamber to the physician's ear. A major obstacle when using Laennec's monaural stethoscope was the tendency of unwanted sounds from the surrounding environment masking the desired sounds, since one ear was directly subject to sounds from the surrounding environment.

A binaural stethoscope was developed by George Camman in 1850 in an effort to overcome or, at least, mitigate the impact of the sounds from the surrounding environment thereby enhancing the ability of the user of the stethoscope to listen to the sounds generated by the heart and other body organs such as the lungs. This stethoscope had flexible tubes which transmitted sound to both ears of the user, reducing the user's exposure to sounds from the surrounding environment.

Both of these stethoscopes employed open-ended sound chambers which, when pressed against the skin of the patient, provided a confined volume of air for transmitting sound waves from the body of the patient to the earpiece. A significant problem with such open-ended stethoscopes is the low intensity of the sound transmitted to the observer's ear(s), due to loss in intensity of the sound as it crosses the interface between the flesh of the patient and the air-filled sound chamber of the chest piece. This signal loss is due to the differences in mechanical impedance of the flesh, which is substantially liquid, and the air employed in the chest piece. This difference in mechanical impedance between the flesh and the air causes only a small portion of the sound wave energy to be transferred from the flesh of the body to the air in the chest piece. As a result, the signal received is low in intensity, and may be difficult to detect or distinguish over ambient noise from the surrounding environment.

Another problem associated with these stethoscopes is that the frequency response of these devices is dependent on the pressure with which the chest piece is applied to the body of the patient. As the pressure applied to the chest piece increases, the chest piece causes distortion of the flesh. This distortion results in the flesh of the patient filling a portion of the chamber and altering the volume and pressure of air in the sound chamber, altering its mechanical performance in amplifying sounds. Thus, the characteristic response of the chest piece is dependent on technique (the touch of the user), so the sounds heard may differ for different users, making comparison of results problematic.

A significant advance in overcoming the problem of low intensity (dB) of the sound transmitted to the user of the stethoscope was made by Dr. R. C. M. Bowles (Massachusetts General Hospital) and was patented in 1901. His improvement to the stethoscope was the addition of a thin semi-rigid diaphragm attached to the chest piece and covering the opening to a conical-shaped sound chamber. This was found to significantly increase the intensity (dB) of sounds generated by the heartbeat and transmitted to the user, achieving such increase by selectively amplifying sounds in the frequency band centered near 90 Hz, the band associated with many of the sounds associated with the heart. The Bowles type stethoscope design is one of the most common currently used, and few significant design changes have been made since its invention.

While the Bowles stethoscope significantly increases the intensity of sounds in the frequency range of many of the sounds generated by the heart, the use of a diaphragm creates frequency-dependent distortion due to the natural vibrational frequencies of the diaphragm. This creates a response which is highly dependent on frequency, having significantly increased sensitivity to sounds in the frequency bands centered at about 90 Hz and 300 Hz, and greatly reduced sensitivity in the frequency band centered near 200 Hz and above about 500 Hz. Thus, while the Bowles type stethoscope offers a significant increase in the intensity (dB) of many of the sounds generated by the heart and other sounds of similar frequency heard by the user of the stethoscope, it reduces the intensity (dB) of transmitted sounds generated by the heart or other organs which are in the frequency bands of reduced sensitivity, thus rendering the resulting stethoscope unsuitable for the observation of many sounds which may be of interest to the user. For this reason, many modem stethoscopes employ a combination chest piece which includes both an open-ended sound chamber, either conical or spherical in shape, and a Bowles type diaphragm-covered conical-shaped sound chamber, enabling the user to select the chamber best suited for monitoring the frequencies of interest.

Furthermore, if the diaphragm of the chest piece receives sounds from the surrounding environment which are in the frequency band of increased sensitivity, these sounds are also amplified, thus tending to obscure the sounds monitored by the user of the stethoscope.

The use of a thin semi-rigid diaphragm also results in a frequency-dependent response of the diaphragm which varies with the pressure on the chest piece as it is engaged with the body. Thus, when a thin semi-rigid diaphragm is employed in a stethoscope, a variation in response of the stethoscope results from the diaphragm changing its natural harmonic frequency as it engages the body. This pressure-dependent variation makes the repeatability of the signals highly dependent on the technique of the user in a manner similar to that of open-chamber stethoscopes, as discussed earlier. The natural harmonic frequency of the thin, semi-rigid diaphragm also introduces transient frequency shifts which can further distort the sound perceived by the user. This is particularly a problem when monitoring impulsive sounds, such as heartbeats.

More recently, in an attempt to improve the quality of sound perceived by the user, electronic stethoscopes have been developed. In electronic stethoscopes the sound waves are converted into an electronic signal by a transducer, which is frequently positioned at the rear or apex of the chest piece sound chamber formed by the horn or cone. This electronic signal is usually amplified and, in some cases, is transmitted to signal conditioning circuits such as electronic filters and/or power amplifiers, which provide the conditioned signal to speakers that form the earpieces. The signal conditioning circuits, when employed, are intended to enhance the quality of the output signal by amplifying the signal intensity of the desired sounds (those sounds being generated by the organ being observed by the user of the stethoscope) and attenuating or filtering out some undesired sounds (from the environment and other organ-generated sounds).

The transducers employed in electronic stethoscopes can be of various types. A classical microphone which is designed to convert airborne sound pressure waves into an electronic signal can be employed for the transducer. The microphone can be placed in the vicinity of the apex of the horn or cone, where it experiences mechanically amplified sound waves, or can be placed in tubes which extend from the chest piece and connect to the earpieces to simulate the characteristic sound reception of a mechanical stethoscope.

While electronic stethoscopes can provide amplified signals, they still suffer from frequency-dependent distortion (particularly when a conventional diaphragm is employed), pressure-dependent distortion, and from sound generated in the environment which reaches the sound chamber of the chest piece. Pressure-dependent variation can be particularly problematic where electronic processing of the received sounds is desired, since the pressure applied by the user can significantly alter the characteristics of the sounds to be processed, making filtering of the noise component difficult. Furthermore, such variation can make electronic recognition and/or analysis of the desired signal component of the sound impractical.

Amplification of the signal in electronic stethoscopes frequently results in amplification of sound from the surrounding in which the stethoscope is operated as well. Because these stethoscopes employ air as the fluid medium transferring sound waves to the transducer, they frequently require substantial amplification to compensate for the signal loss caused by limited transfer of the sound wave energy from the flesh to the transducer. If the intensity (dB) of the sound from the surroundings in the unamplified sound transmitted through the sound chamber is sufficiently great as to mask the sound generated by the organ of interest, simply amplifying the electronic signal produced by the transducer does not allow the sound emanating from the organ to be monitored.

There have been various attempts to reduce exposure of the sound chamber to sounds from the surrounding environment by providing covers on the chest piece to prevent airborne sounds being transmitted through the sound chamber to the transducer. U.S. Pat. No. 4,995,473 and 5,578,799 teach two examples of such covers.

In addition to sounds generated by the surrounding environment being transmitted through the sound chamber, another problem has been that movement of the chest piece over the skin of the patient generates sounds which are subject to amplification. These sounds may not only obscure the sounds of interest, but also may be of sufficient intensity as to cause discomfort to the user.

An alternative approach to enhance the performance of an electronic stethoscope is to employ a confined volume of liquid to transmit the sounds from the body to the transducer. This technique is beneficial in that it reduces the signal loss due to mechanical impedance by employing a liquid rather than air to transmit the sound waves to the transducer. U.S. Pat. No. 3,130,275 teaches the use of a piezoelectric transducer in combination with a cylindrical cavity to transmit the body sounds, the liquid being confined in the cavity by a membrane. U.S. Pat. No. 3,076,870 teaches the use of a capacitance transducer in combination with a liquid confined between the capacitor and a membrane. While the '870 patent indicates that the liquid has "damping" capacity for attenuating "unwanted external sounds", to a large degree the external sounds attenuated would be in the higher frequency range, greater than about 1,000 Hz. Thus, the liquid would not substantially reduce the lower frequency sound, which is often a large component of the unwanted external sound.

A further problem with all stethoscopes that has not previously been appreciated is that "unwanted external sounds" can also be indirectly transmitted though the membrane, since the body provides a conduction path for these "unwanted external sounds". Even in liquid-filled chest pieces, it is felt that such conducted unwanted sounds would not be effectively attenuated, independent of their frequency. This latter source of unwanted external sounds is particularly a problem in monitoring patients in high-noise environments, such as during transport where vehicle noise due to sirens, aircraft engines, helicopter rotors, etc. can be sufficiently loud as to mask the desired signals from the body. Since such transport often occurs in emergency situations where monitoring is necessary to providing prompt diagnosis and treatment, this deficiency of existing devices is a serious limitation.

Thus, there is a need for a chest piece which provides signals with reduced noise, including reduction of noise transmitted through the body.

OBJECTS OF THE INVENTION

It is an object of the invention to detect sound (body signals) generated by an animate human body and transmit these signals to a transducer without distortion or other artifacts.

It is another object of the invention to reduce the ambient noise sensed by the transducer of a chest piece.

It is another object of the invention to provide a stethoscope with a "flat frequency response curve", defined as a curve where perceived intensity (dB) of sounds is not strongly dependent on their frequency (Hz), and which avoids the introduction of resonant frequency bands.

It is another object of the invention to provide a stethoscope having reduced transient response to received sounds.

It is another object of the invention to provide a body signal transducing device with reduced sensitivity to noise which is transmitted through the body.

It is still another object of the invention to provide a body signal transducing device that is immune to noise due to slight movement on the skin surface.

It is a further object of the invention to provide a stethoscope where the response is not dependent on the pressure with which the sensor is applied to the skin.

It is yet another object of the invention to provide a mechanical waveguide for a stethoscope to reduce the intensity of sound waves that propagate along paths which are not normal the skin of the body under observation.

SUMMARY OF THE INVENTION

The present invention is a chest piece which is suitable for use in a stethoscope having, in addition to the chest piece, earpieces which are operably connected to the chest piece by a transmission medium.

In an elementary form, the chest piece has a housing having a cavity which acts as a sound chamber. The cavity has a cavity surface which is a surface of revolution generated by a parabola having a parabola apex, a parabola focal point, and a parabola axis. The parabola is rotated about the parabola axis to generate the cavity surface such that the cavity surface is formed as a paraboloid, having a paraboloid apex coincident with the parabola apex, a paraboloid axis coincident with the parabola axis, and a paraboloid focal point coincident with the parabola focal point. The cavity of the housing is further configured such that the paraboloid focal point resides in the cavity and the cavity is terminated by the paraboloid apex and a substantially planar opening which is substantially normal to the paraboloid axis.

A transducer is provided for converting received sound into an electronic signal. Means for positioning the transducer at or near the paraboloid focal point are provided. In one embodiment of the invention, a tube that pierces the paraboloid apex of the paraboloid can be employed as the means, while in another embodiment the transducer can be supported by a spider-leg support which is secured to the cavity surface can serve as the means.

The parabolic shape of the cavity surface acts to reflect sound waves transmitted normal to the substantially planar opening (those sound waves generated by the area of the body to which the chest piece is applied) to the transducer at the focal point, while reflecting sound waves which are substantially inclined to the substantially planar opening (both unwanted sound waves generated externally and transmitted through the body and unwanted sound waves generated in other areas of the body, collectively noise) away from the focal point, thereby reducing the intensity of the noise at the location of the transducer.

It is further preferred that a support structure be provided that extends across the substantially planar opening and is substantially transparent to sound. It is further preferred that the support structure be a substantially open support structure configured to provide a series of passages therethrough, where the passages extend parallel to the paraboloid axis.

The series of passages thus form a mechanical wave guide which reflects sound waves that are not propagating substantially parallel to the paraboloid axis.

While the above described chest piece is effective in reducing the intensity of noise, it is preferred that a membrane be provided, which covers the substantial planar opening of the cavity to form to a closed cavity. Preferably, the membrane is fabricated from a compliant material which has mechanical properties similar to human skin. This match is preferably accomplished by coordinating the selection of size, thickness, and composition of the membrane such that the membrane is essentially acoustically transparent, having a first mode natural frequency which is well below that of the signals to be monitored. Having the first mode natural frequency so selected reduces cancellation of the sounds of interest due to the natural frequency of the membrane, as well as excitement of these frequencies by the sounds of interest which could create transient effects and effectively make the output of the chest piece time dependent. Preferably, to minimize these problems, the first mode natural frequency of the membrane is preferably less than about 20 Hz. An example of a suitable material for the membrane would be a high strength, low durometer, molded polyurethane elastomer compound. It is also preferred that the membrane have a high coefficient of friction, to minimize the likelihood of sliding on the skin surface which would introduce noise which might be sensed by the chest piece. The membrane is preferably held in position with a bezel which attaches to the housing.

It is also preferred that the membrane be configured so as to provide a concave surface when viewed from the focal point of the parabola, thus being convex when viewed by the user. The convex shape helps assure that, when the membrane is placed against the skin of a patient, no air pockets which might adversely affect the response are trapped between the membrane and the skin. When the cavity is gas filled, the membrane may be maintained in a convex configuration by maintaining the pressure in the cavity slightly above atmospheric pressure. Alternatively, when substantially open support structure is employed, it can be made convex in form to support the membrane. Again, such a support structure is preferably configured to also provide a mechanical wave guide.

Preferably, the cavity is filled with a non-gaseous fluid, which is substantially incompressible and which fills the chamber such that the resulting membrane has a convex surface and thus the volume of the fluid remains constant. As used herein, the term fluid includes both liquids and semi-solid colloidal solutions, hereinafter referred to as gels. It is further preferred that a gel be employed, to reduce the likelihood of leakage in the event that the membrane is punctured. A gel is also preferred so that the membrane need not support the fluid, thus allowing the membrane to be thinner and have a lower modulus of elasticity than would be required if the membrane needed to support the fluid.

When a liquid or gel is employed in the cavity as a sound transmission medium, it is selected to have physical characteristics similar to those of human flesh, which is typically similar to the properties of water, so that the acoustical impedance matches that of the flesh. It is further preferred that the sound transmission medium be equal to or slightly lower in mechanical impedance than the flesh. A silicone gel is preferred for having physical properties that are not strongly temperature dependant over a wide range of temperatures.

A variety of transducers can be employed such as capacitance transducers, piezoelectric transducers, microphones, and hydrophones; however, it is preferred that when the cavity is gas-filled, the transducer is a microphone, and in the case that the cavity is liquid or gel-filled, a hydrophone is preferably employed as the transducer. When a microphone is employed, the microphone is preferably an omni-directional electret type (cardioid) microphone to respond to both direct sound waves and sound waves reflected from the parabolic cavity surface of the chest piece. When a hydrophone is employed, it is preferred that it be omnidirectional in its response.

When a transducer having a substantially planar sound receiving surface is employed as the transducer in the chest piece, it is preferred that the parabolic cavity surface be contoured such that the transducer, which is at or near the focal point of the parabola, is in close proximity to the substantially planar opening and that the transducer be mounted on a spider-leg support such that the substantially planar sound receiving surface has an unobstructed view of the apex of the paraboloid. It is further preferred that a supplemental transducer be provided, the transducer mounted at or near focal point of the paraboloid serving as a primary transducer. The supplemental transducer is mounted between the primary transducer and the membrane or, when a mechanical wave guide is provided, the supplemental transducer is mounted between the primary transducer and the mechanical wave guide. The supplemental transducer serves to receive sound blocked from reaching the cavity surface by the primary transducer. The supplemental transducer is preferably positioned in close proximity to the paraboloid focal point to minimize the phase difference between the sound received by the two transducers. Furthermore, when the supplemental transducer has a substantially planar sound receiving surface, this surface is positioned substantially normal to the paraboloid axis and facing the membrane and/or the mechanical wave guide.

To further improve the directional response of the chest piece having a liquid- or gel-filled sound cavity, it is also preferred that a mechanical wave guide such as discussed above be employed. The mechanical wave guide is positioned between the membrane and the transducer. While the mechanical wave guide can have a convex surface which supports the membrane, this support is not needed to maintain the convex contour of the membrane, since the liquid or gel maintains pressure against the membrane to maintain its convex profile. Since such support is not needed, it is preferred that mechanical wave guide be in close proximity to but spaced apart from the membrane. Having the mechanical wave guide so positioned reduces the influence of the mechanical wave guide on the movement of the membrane and allows the membrane to more readily comply to any irregularities of the flesh on which it is placed.

In all applications, the support structure/mechanical wave guide is preferably constructed from a rigid material such as aluminum or a semi-rigid plastic material (polycarbonate, ABS, or similar engineering grade plastic). The mechanical wave guide preferably has a thickness of at least about ⅛ inch (3 mm) and has an array of parallel sound passages extending therethrough.

While the frictional nature of the membrane is preferably sufficient to prevent inadvertent motion of the chest piece across the skin of the patient under normal use, to further reduce the possibility of noise due to motion of the chest piece across the skin, it is preferred for the stethoscope to be activated by a pressure switch. The pressure switch responds to fluid pressure inside the cavity, and only allows the stethoscope to activate when the pressure is sufficient to assure that the membrane of the chest piece is firmly applied to the skin. This firm pressure, in combination with the frictional nature of the membrane, is sufficient to prevent any noise generated by motion of the chest piece across the skin. The pressure switch is preferably connected in series with a manual switch, and interrupts power to one or more of the transducer, the transmission medium, or the earphones.

BEST MODE OF CARRYING THE INVENTION INTO PRACTICE

Figure 1:
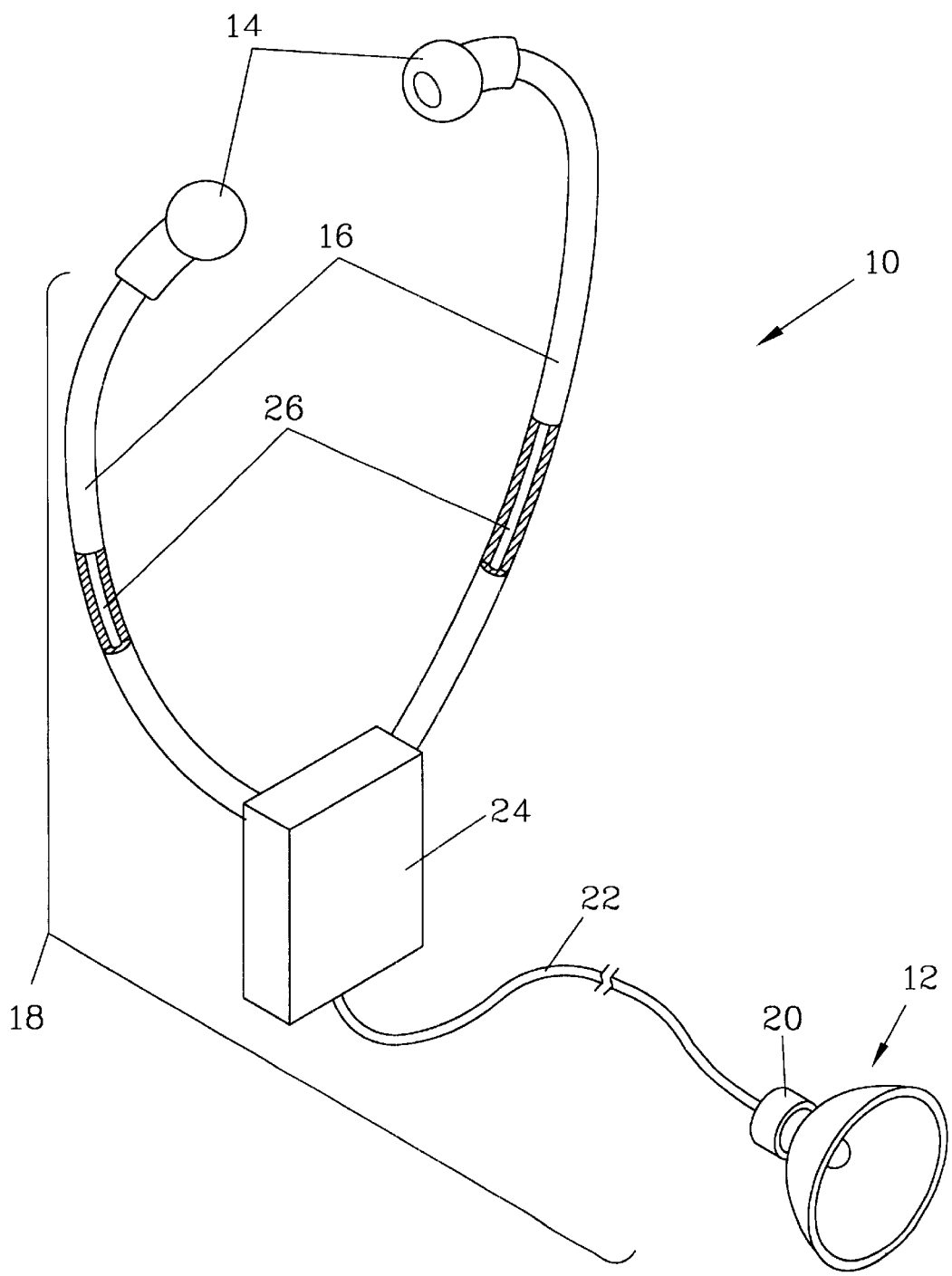
FIG. 1 is an isometric view of an electronic stethoscope which incorporates the chest piece of the present invention. The stethoscope has a transmission medium which includes a pre-amplifier which is integral with the transducer. to a pre-amplified signal, which in turn is transmitted to a signal processing unit via chest piece wires. The signal processing unit in turn may perform a variety of tasks, such as filtering and further amplifying the signal to provide a processed signal which is transmitted by ear phone wires to earphones which are configured to engage the ear canals of the user.

FIG. 1 is an isometric view of a stethoscope 10 which incorporates a chest piece 12 which forms one embodiment of the present invention. The chest piece 12 is designed for placement on the flesh of the body of a patient (not shown) to receive sounds generated in the body. For example, when the heart of the patient is being monitored, the chest piece 12 is placed on the chest over the heart such that the sound generated by the heart propagates sound waves that are directed into the chest piece 12. While this is one use of the chest piece 12, it has many alternate uses such as monitoring the lung function and the pulse rate. The stethoscope 10 also has earphones 14 which, for the stethoscope 10 illustrated, are configured to fit the ear canal of the user (not shown), allowing the user to hear the sounds being sensed by the chest piece 12. The earphones 14 are maintained in contact with the ear canal by resilient tubes to which the earphones 14 are attached. The chest piece 12 is connected to the earphones 14 via an electronic transmission system 18. The transmission system 18 frequently includes a pre-amplifier 20, which can be an integral part of the chest piece 12 and provides an amplified signal which is transmitted through chest piece wires 22 to a signal processing unit 24. Depending on the details of the signal processing unit 24, it can provide various functions such as filtering the signal and amplifying the signal. The processed signal is then supplied to the earphones 14 via earphone wires 26 which complete the electronic transmission system.

Figure 2:
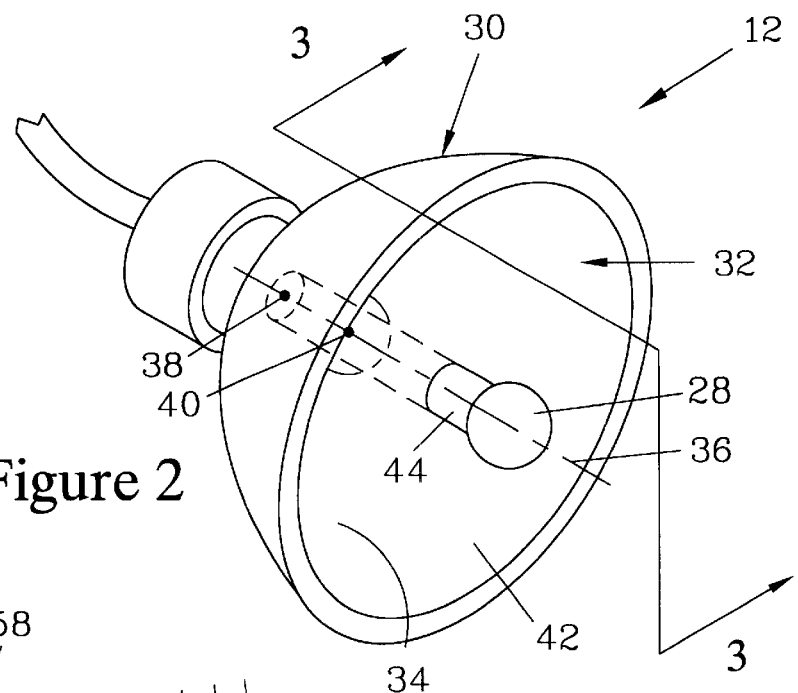
FIG. 2 is an exploded isometric view of the chest piece shown in FIG. 1, illustrating a housing with a cavity which has a cavity surface defined by revolution of a parabola about a parabola axis of symmetry, thus generating a paraboloid having a focal point and a paraboloid axis which is coincident with the parabola axis. The cavity has a substantially planar opening which is substantially normal to the paraboloid axis. A microphone which serves as a transducer is positioned at the paraboloid focal point.
Figure 3:
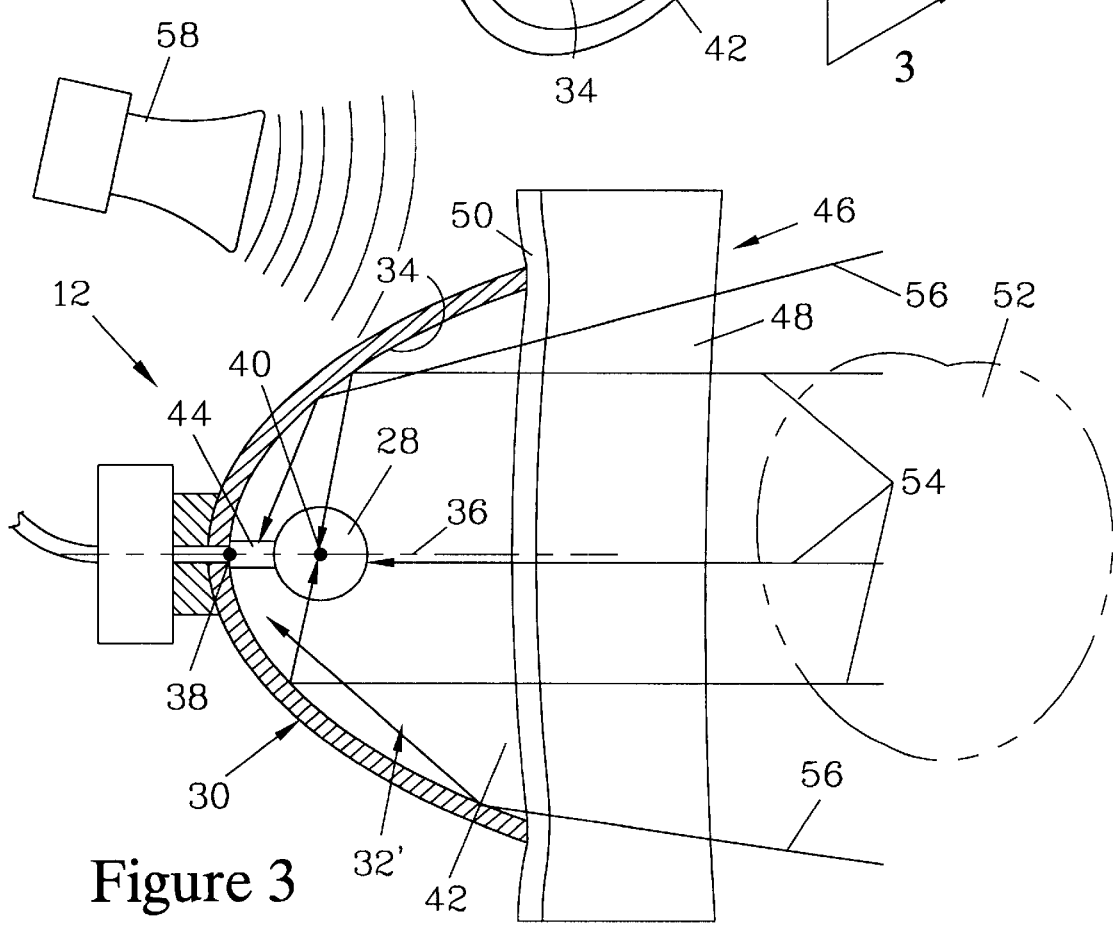
FIG. 3 is a view of the section 3—3 of FIG. 2, showing the assembled chest piece when it is engaged with the flesh of a patient and positioned to detect the heartbeat of the patient.

FIGS. 2 and 3 more fully illustrate the elements of the chest piece 12 shown in FIG. 1. The chest piece 12 has a microphone 28 which, in this embodiment, is an air-activated omnidirectional electret type ("cardioid") microphone, and serves as a transducer to convert sounds emitted from the body into an electrical signal. One such microphone suitable for this application is the model ELM 22, commercially available from TELEX.

As shown in FIG. 2, the chest piece 12 has a housing 30 having a cavity 32 therein. The cavity 32 has a cavity surface 34 that is generated by rotation of a parabola about its axis of symmetry. The resulting cavity surface 34 is a paraboloid having a paraboloid axis 36, a paraboloid apex 38 and a paraboloid focal point 40. The cavity 32 terminates at the parabolic apex 38 (shown in FIG. 3) and in a substantially planar opening 42 which is substantially normal to the parabolic axis 36. The substantially planar opening 42 is positioned such that the paraboloid focal point 40 resides in the cavity 32.

The microphone 28 is mounted on a pedestal 44 which attaches to the parabolic apex 38 of the cavity 32. The pedestal 44 serves to maintain the microphone 28 at the parabolic focal point 40. These features are best shown in FIG. 3, which also illustrates the chest piece 12 positioned against flesh 46, which is composed of tissue 48 having a viscosity similar to that of water and terminating in skin 50.

As illustrated in FIG. 3, the chest piece 12 is positioned to monitor a heart 52 of a patient. For such an application, it is beneficial to have the heart 52 in close proximity to the chest piece 12 to minimize the path of the sound generated by the heart 52 as it passes through the flesh 46, thereby minimizing the attenuation of sounds generated by the heart 52. When such conditions are met, the heart 52 is aligned with the paraboloid axis 36 and the sound generated by the heart 52 propagates in a direction indicated by vectors 54 which are substantially parallel to the paraboloid axis 36. The pressure applied to the chest piece 12 by the user is sufficient to assure that the skin 50 sealably engages the substantially planar opening 42 of the chest piece 12. Having the chest piece 12 so positioned provides a closed cavity 32' with a fixed quantity of air therein. The closed cavity 32' has a volume which is slightly reduced from the volume of the open cavity 32, since the flesh 46 occupies a small fraction of the closed cavity 32'. The air confined in the closed cavity 32' is responsive to sounds which enter the closed cavity 32'.

Since the cavity surface 34 is formed by a paraboloid with an paraboloid axis 36 and the heart sounds traverse a path represented by the vectors 54 which are parallel to the paraboloid axis 36, these sounds are reflected by the cavity surface 34 to the paraboloid focal point 40 and are captured by the microphone 28 which resides at the focal point 40. On the other hand, those sounds propagating from other sources, where the propagation as is illustrated by the vectors 56, are not parallel to the paraboloid axis 36 and, upon reflection, are directed away from the paraboloid focal point 40 and thus not part of the sound received by the microphone 28. These excluded sounds can either originate in other regions of the body or can originate outside the body, such as sounds from a siren 58 which are subsequently transmitted through the flesh 46. With the above described geometry, one obtains a benefit not heretofore available in chest pieces and not readily obtainable through signal processing systems.

To match the experience of the stethoscope user, the chest piece 12 is preferably similar in size to that of a conventional stethoscope. The substantially planar opening 42 preferably has a diameter of about 1–2 inches (25–51 mm), since a larger diameter might create difficulties in creating a satisfactory seal between the substantially planar opening 42 and the skin 50. The depth of the cavity 32 and the distance from the cavity surface 34 to the paraboloid focal point 40 is determined, in part, by the dimensions of the microphone 28 which must be accommodated therein. However, it is also desirable to limit the volume of air in the cavity 32, since a smaller volume of air increases sensitivity of the chest piece 12 by reducing the volume of air which must be excited by the sound waves received. It should be noted that the parabolic shape of the housing 30 is somewhat exaggerated in the figures for purposes of illustration.

Figure 4:
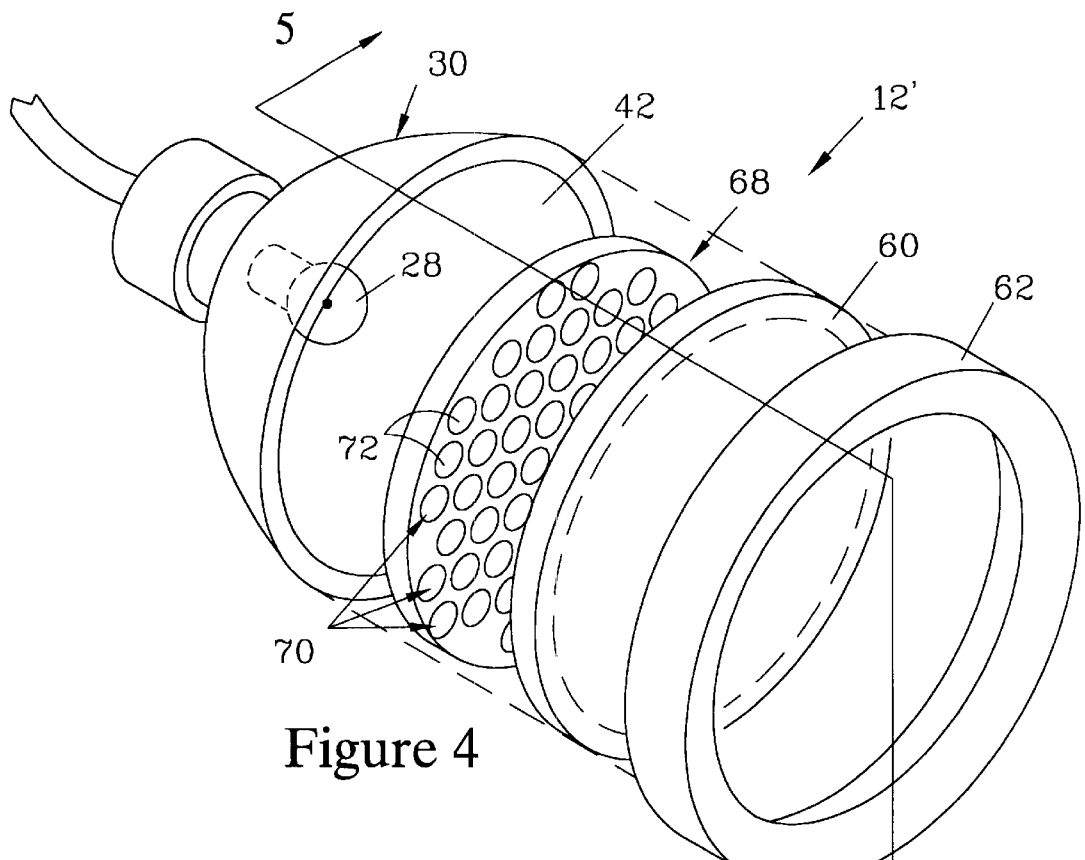
FIG. 4 is an exploded isometric view of another chest piece suitable for use in a stethoscope such as illustrated in FIG. 1. The cavity of the chest piece is air-filled, as is the chest piece shown in FIGS. 2 and 3, but in this embodiment a membrane is provided which covers the substantially planar opening, as well as a membrane support structure which supports the membrane and also serves as a wave guide to substantially attenuate sounds which traverse paths which are not parallel to the paraboloid axis.
Figure 5:
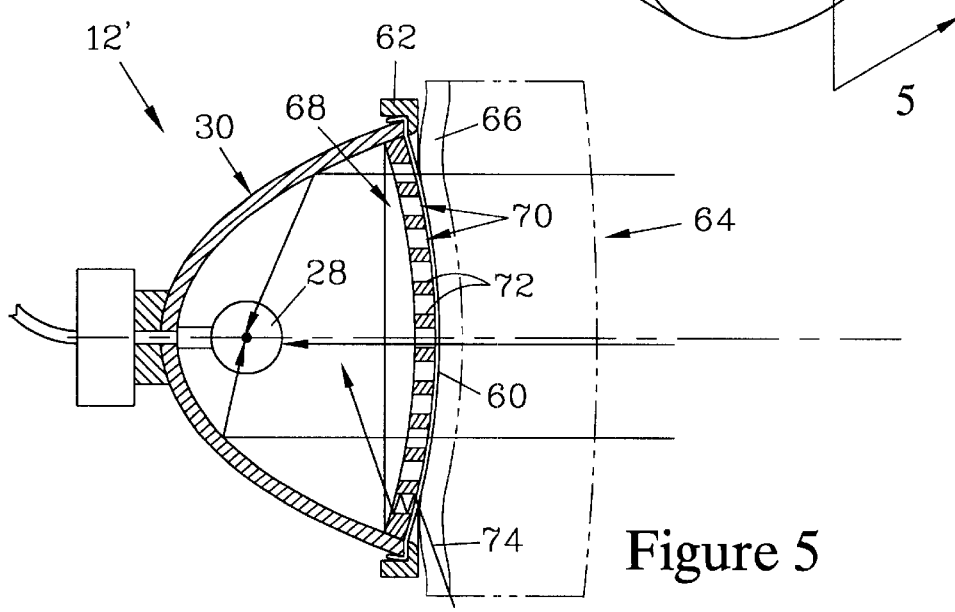
FIG. 5 is an assembled view of the section 5—5 of the chest piece of FIG. 4, showing the position of the microphone in the cavity formed by the paraboloid and its relationship to the apex, focal point, and axis of the paraboloid. The chest piece is shown in contact with the flesh of a patient's body. The figure also illustrates the convex profile of the membrane support structure, which serves both to support the membrane and as a mechanical wave guide. The membrane support structure maintains the membrane in a convex surface configuration when viewed from the flesh that it engages, and this helps assure that, as the chest piece is brought into contact with the flesh of the body, the skin gradually advances across the membrane so as to avoid air entrapment between the skin and the membrane. A bezel secures the membrane over the substantially planar opening and maintains the mechanical wave guide in place.

FIGS. 4 and 5 illustrate an embodiment of a chest piece 12' which is similar to the chest piece 12 of the embodiment shown in FIGS. 2 and 3, in that it contains all the elements of the chest piece 12. It differs in part by having a membrane 60 which covers the substantially planar opening 42, and a bezel 62 which attaches to the housing 30 and maintains membrane 60 in position. Means are provided to assure that the membrane 60 maintains a convex configuration when viewed looking toward the chest piece 12'. Having a convex membrane 60 assures positive contact with the flesh 64 (shown in phantom) of a patient's body and prevents entrapped air pockets between the skin 66 and the membrane 60 which might adversely affect transmission of the sound waves. The membrane is preferably a high strength, low durometer, molded polyurethane elastomer compound, such as a 45–50 Shore A Durometer Elastomer.

The convex shape of the membrane 60 can be maintained by a variety of means when the cavity 32 is gas filled. One means of assuring a convex surface is to maintain the gas pressure in the cavity 32 greater than the atmospheric pressure. However, it is preferred to employ a membrane support structure 68 which has sufficient structure to support the membrane 60 in its convex configuration, and yet provides a sufficient number of passages 70 to transmit sound therethrough and assure that the resulting structure does not have a resonance frequency in the wavelengths of interest. It is further preferred that the passages 70 be configured and positioned such that they provide a mechanical wave guide for the sound which reaches the membrane support structure 68. The membrane support structure 68 should have thickness of about at least ⅛ inch (3 mm) and the passages 70 should have sidewalls 72 which are substantially parallel to the paraboloid axis 36.

The inclusion of the series of passages 72 through the membrane support structure 68 allows the membrane support structure 68 to act as a mechanical wave guide. When functioning as a mechanical wave guide, the membrane support structure 68 enhances the quality of sound provided to the user from the chest piece 12' by eliminating some of the unwanted sounds reaching the microphone 28. Vector 74 is a schematic representation of the widely divergent path traveled by a sound from a region of the body other than the region where the chest piece 12' is placed. Such sounds do not pass through the membrane support structure 68, but rather are subject to multiple reflections as they proceed down the passages 72. Due to the multiple reflections, any components of such sounds which reach the microphone 28 are likely to be out of phase, and may result in cancellation.

Figure 6:
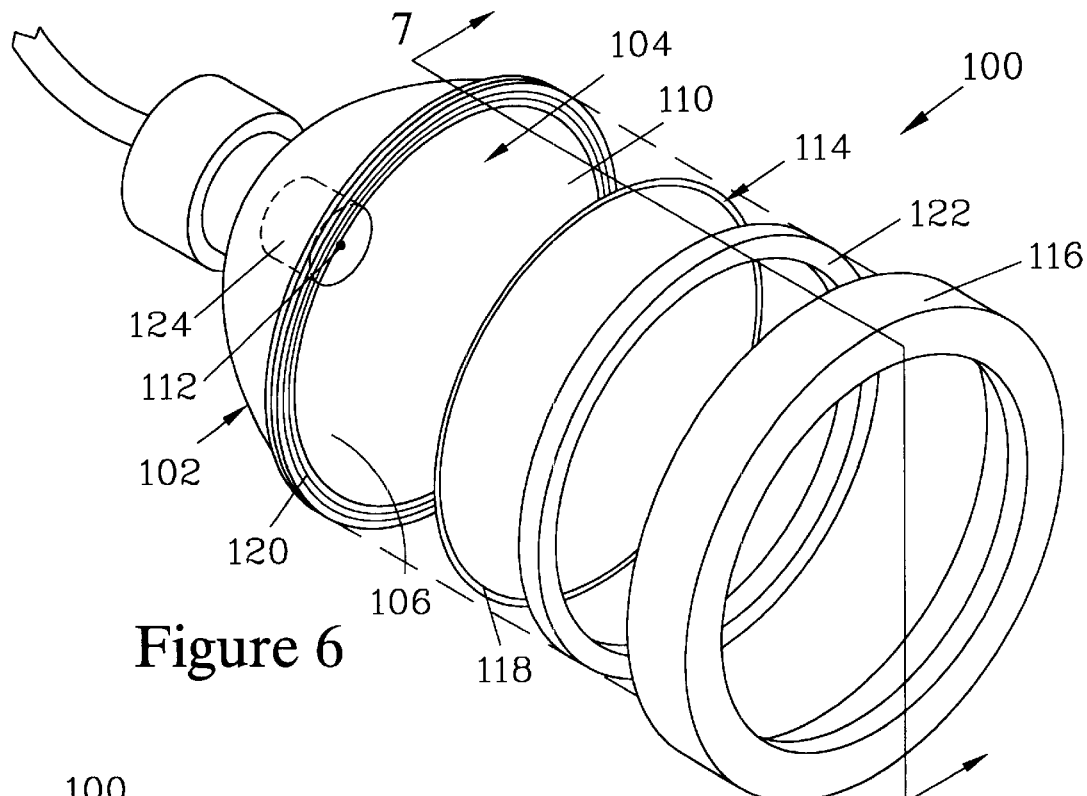
FIG. 6 is an exploded isometric view of a chest piece for another embodiment of the present invention. This chest piece has many features in common with the chest piece shown in FIGS. 4–5. However, in this embodiment the cavity is filled with a non-gaseous fluid medium, either a substantially incompressible liquid or a substantially incompressible gel. The transducer in this embodiment is a hydrophone, which is embedded in a pedestal assembly.

FIG. 6 is an exploded isometric view of a chest piece 100 which forms another embodiment of the present invention. This embodiment provides improved mechanical coupling between sounds transmitted through the flesh (not shown) and the chest piece 100, thus reducing attenuation of the sound waves generated by the organ of interest. The chest piece 100 shares many features in common with the chest piece 12' illustrated in FIGS. 4 and 5. The chest piece 100 has a housing 102 having a cavity 104 that is bounded by a cavity surface 106. The cavity 100 is terminated by a paraboloid apex 108 and by a substantially planar opening 110. The cavity surface 106 is defined by the paraboloid having a paraboloid focal point 112 residing in the cavity 104. A membrane 114 covers the substantially planar opening 110 and is held in place by a bezel 116 so as to provide a seal for the cavity 104, which is either liquid-filled or gel-filled.

In this embodiment, the membrane 114 is preferably formed of an elastomer such as a polyurethane compound, having a small thickness and low modulus of elasticity so as to be substantially acoustically transparent to sound waves greater in frequency than about 20 Hz. The use of a thin, low modulus material for the membrane 114 avoids the problems of frequency-dependent distortion due to resonance of the membrane 114, as occurs in chest pieces which employ a semi-rigid diaphragm. When the cavity 104 is liquid filled, it may be desirable to reinforce the membrane 114 with nylon threads to support the weight of the liquid, although this may effectively raise the modulus of elasticity of the membrane 114. However, if sufficiently spaced apart, such threads may not impede the transfer of the sound waves. The membrane 114 of this embodiment is formed with a beaded rim 118, which engages a groove 120 in the housing 102 which encircles the substantially planar opening 110. The bezel 116 and the housing 102 are both threaded, and the bezel 116 screws onto the housing 102 to secure the membrane 114 in position. Since the membrane 114 is preferably of a material having a high coefficient of friction, rotation of the bezel 116 during assembly would be likely to dislodge the membrane 114 from the groove 120. To prevent this, a bearing ring 122 is interposed between the membrane 114 and the bezel 116.

While the cavity 104 in this embodiment may be filled with a variety of non-gaseous media such as a substantially non-compressible liquid which can maintain the membrane 114 with a convex surface, it is preferred for the medium to be a gel, since a gel reduces any chance of leakage in the event that the membrane 114 is punctured. Additionally, a gel can be molded so as to maintain the membrane 114 in a convex shape, facilitating fabrication and eliminating any requirement for the membrane 114 to be self-supporting. In either case, the liquid or gel should have an acoustical impedance that is equal to or slightly less than that of human flesh to enhance mechanical transfer of sound waves from the body of the patient to the non-gaseous medium.

Since the cavity 104 is filled with a gel or liquid, a conventional microphone can not be used as the transducer. For this embodiment, a hydrophone 124 serves as a transducer, and is located at or near the paraboloid focal point 112, where it receives sound waves transmitted through the non-gaseous medium contained in the cavity 104. The hydrophone 124 can be any of a variety of devices designed to convert sound waves in a non-gaseous medium into an electrical signal or, if a commercial hydrophone of sufficiently small size is not available, a conventional microphone can be converted to a hydrophone by sealing it into an envelope impervious to the non-gaseous medium to prevent ingress of the non-gaseous medium. One manner of sealing which has been found effective is to wrap a microphone in an impermeable material which is substantially acoustically transparent, such as the material employed for the membrane 114. Preferably, the hydrophone 124 has a "cardioid" field of sensitivity to receive both sound waves which are transmitted directly to the hydrophone 124 as well as sound waves reflected by the cavity surface 106.

Figure 7:
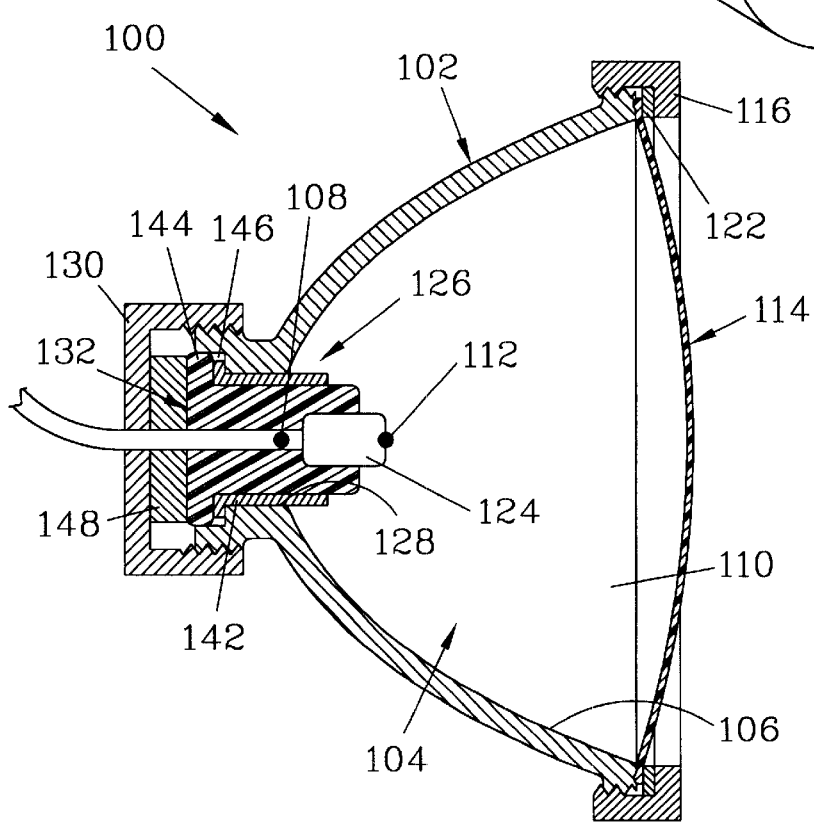
FIG. 7 is an assembled view of the section 7—7 of FIG. 6 which illustrates the membrane having a convex surface which is so maintained by the liquid or gel contained in the cavity.
Figure 8:
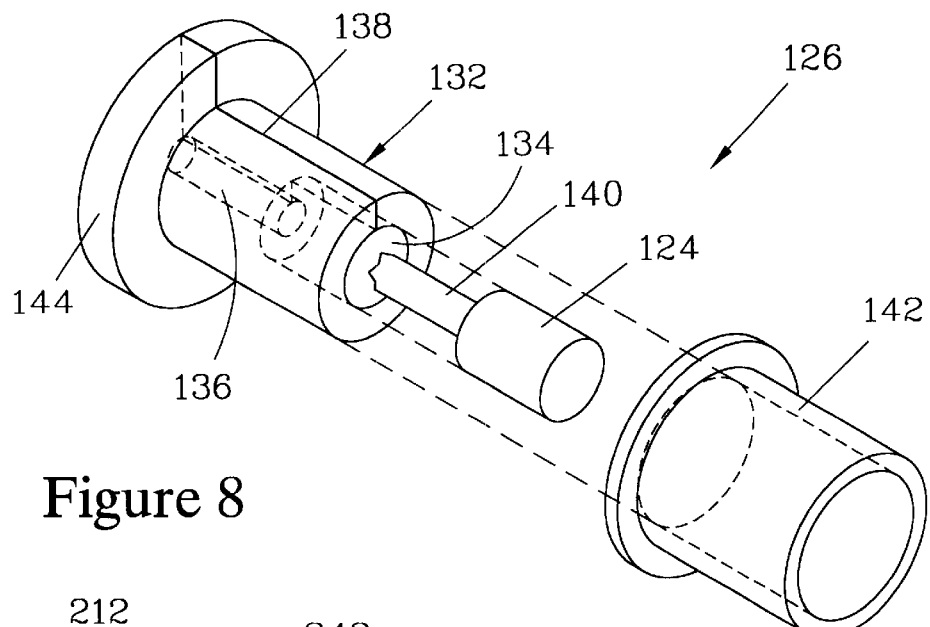
FIG. 8 is an exploded isometric view of the pedestal assembly and hydrophone shown in FIG. 6.

In the chest piece 100, a pedestal assembly 126 is employed to maintain the hydrophone 124 at the focal point 112, as shown in FIGS. 7 and 8. A passage 128 in the apex 108 of the paraboloid is provided into which the pedestal assembly 126 slides and is held in place by a cap nut 130 which threadably engages the housing 102. The pedestal assembly 126 illustrated has a hydrophone casing 132 (best shown in FIG. 8), which is formed with a hydrophone recess 134 and a lead passage 136. To facilitate assembly, the hydrophone casing 132 has a slit 138 to allow the hydrophone 124 and an associated hydrophone lead 140 to be placed respectively into the hydrophone recess 134 and the lead passage 136. The hydrophone casing 132 is preferably formed of a substantially resilient, deformable material, with the hydrophone recess 134 and the lead passage 136 preferably being somewhat undersized. A 20–25 Shore A Elastomer has been found to be effective for the hydrophone casing 132. When the hydrophone casing 132 is force-fitted into a rigid mounting sleeve 142, it is compressed such that the hydrophone recess 134 forcibly and sealably engages the hydrophone 124, and the lead passage 136 forcibly and sealably engages the hydrophone lead 140 to prevent leakage around the hydrophone 124 and the hydrophone lead 140. The size of the hydrophone casing 132 with respect to the rigid mounting sleeve 142 is such that, as the hydrophone casing 132 is forced into the rigid mounting sleeve 142 during assembly, the slit 138 is forced closed by compression of the hydrophone casing 132.

To complete sealing of the cavity 104 and prevent leakage of the non-gaseous medium, the hydrophone casing 132 has a sealing flange 144 which sealably engages a flange-engaging recess 146 in the housing 102. The hydrophone casing 132 is forced into engagement with the housing 102 by a force ring 148 which in turn is engaged by the cap nut 130. The deformable nature of the hydrophone casing 132 not only facilitates the construction of a sealed assembly, but also serves to damp mechanical vibrations, thus reducing noise due to such vibrations on the hydrophone 124.

Figure 9:
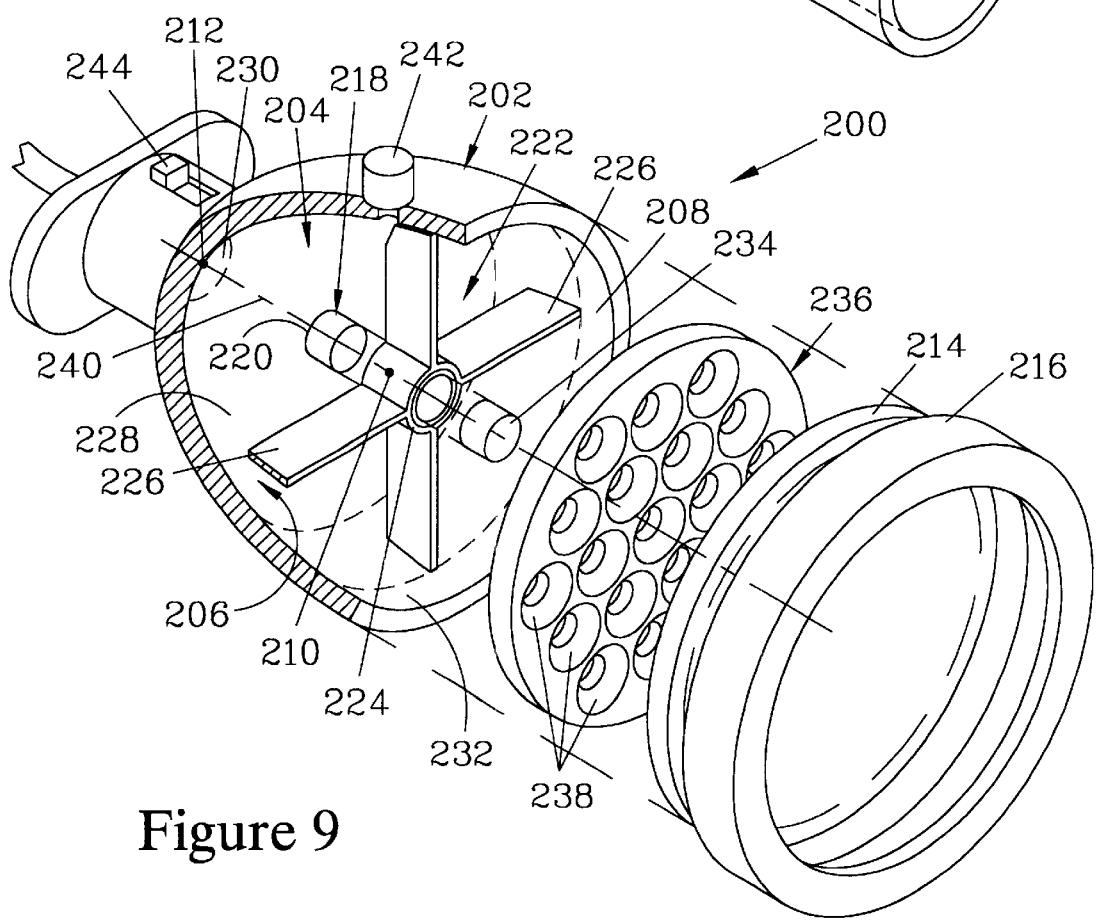
FIG. 9 is an exploded isometric view of a chest piece for another embodiment of the present invention, which has many features in common with the chest piece shown in FIG. 6, but which differs in several respects. The chest piece has a mechanical wave guide positioned in close prolixity to the substantially planar opening but sufficiently spaced apart from the membrane covering the substantially planar opening to avoid possible impediment of its movement responsive to the motion of the skin. The embodiment of FIG. 9 also differs in that the focal point of the paraboloid is at a substantial separation from the apex of the paraboloid which forms the cavity surface. This geometry is designed to better suit the character of the transducer, which in this embodiment has a substantially planar sound receiving surface. This surface is positioned to be responsive to sound waves reflected from the region of the parabolic cavity surface associated with the paraboloid apex. Such a transducer with a substantially planar sound receiving surface, which serves as a primary transducer, could result from the use of either a piezoelectric or capacitance transducer. In this embodiment, a supplemental transducer, also having a substantially planar sound receiving surface, is provided and is positioned between the primary transducer and a mechanical wave guide. A pressure switch is also provided, which activates the transducers in response to the pressure in the cavity.

FIG. 9 is an exploded isometric view of a chest piece 200 which forms another embodiment of the present invention. The chest piece 200 again has a housing 202 with a cavity 204 bounded by a cavity surface 206 and terminating in a substantially planar opening 208. The cavity surface 206 bounds a paraboloid having a paraboloid focal point 210 and a paraboloid apex 212. In this embodiment, the paraboloid focal point 210 is positioned at a substantial distance from the paraboloid apex 212 and in close proximity to the substantially planar opening 208. A 2D membrane 214 covers the substantially planar opening 208 and is held in place by a bezel 216. The cavity 204 is filled with a gel.

The change in the geometry of the paraboloid from that of the embodiment of FIGS. 6–8 has been made to accommodate a transducer which has reception characteristics which differ from the omni-directional hydrophone of the embodiment of FIGS. 6–8. In this embodiment, a primary transducer 218 is employed which has a substantially planar sound reception surface 220. The primary transducer 218 is positioned at or near the paraboloid focal point 210, and is preferably a hydrophone. The substantially planar transducer 218 is supported by a spider-leg support 222 having a central body 224 and radial extending legs 226 attached to the cavity surface 206. The sound reception surface 220 of the primary transducer 218 is directed towards the paraboloid apex 212. The sound reception surface 220 receives the reflected sounds from a rearward reflecting region 228 of the cavity surface 206, diminished by a shadowed region 230 which is blocked from reception of sound by the primary transducer 218. A portion of the region of the paraboloid surface which has been lost as an effective reflecting surface (the shadowed region 230 and a forward reflecting region 232 of the paraboloid) can be reclaimed by employing a supplemental transducer 234, preferably having acoustical performance comparable to that of the primary transducer 218. The supplemental transducer 234 is also mounted on the spider-leg support 222, but is positioned such that it is directed towards the substantially planar opening 208. Thus, the primary transducer 218 receives sound waves that are predominantly reflected by the cavity surface 206, while the supplemental transducer 234 receives predominantly sound waves which are transmitted from the membrane 214. Since the supplemental transducer 234 receives predominantly sounds from the membrane 214, a mechanical wave guide 236 is provided between the membrane 214 and the supplemental transducer 234 to filter the incoming sound and limit the received sound to the portion of the sound which is traversing a path substantially normal to the membrane 214. The mechanical wave guide 236 has an array of sound passages 238 which are parallel to a paraboloid axis 240 which is the axis of symmetry of the cavity 204. The sound passages 238 allow sound waves which are parallel to the paraboloid axis 240 (and thus normal to the membrane 214) to readily pass through the mechanical wave guide 236, while reflecting those sound waves which are not parallel.

Another improvement of the chest piece 200 resides in a pressure switch 242. The pressure switch 242 is mounted to the housing 202 so as to be responsive to changes in pressure of the medium in the cavity 204. The pressure switch 242 only allows activation of the chest piece 200 when the pressure is equal to or exceeds a predetermined value. In this embodiment, the pressure switch 242 controls activation of the transducers (218, 236). When the chest piece 200 is incorporated into a stethoscope such as that shown in FIG. 1, the pressure switch 242 could control activation of the earphones 14 or the electronic transmission system 18.

When the membrane 214 of the chest piece 200 is pressed against the skin of a patient, the convex shape of the membrane 214 is deformed, increasing the pressure in the cavity 204. The pressure value for activation of the pressure switch 242 is chosen such that the pressure switch 242 is only activated when the membrane 214 is pressed against the skin with sufficient force that friction between the skin and the membrane 214 prevents motion of the membrane 214 across the skin. Setting the pressure for activation of the switch at a pressure of about 2 to 4 ounces (0.6 to 1.1 N) is felt to be practical. Thus, noise due to such motion only occurs when the stethoscope is inactive, and is not perceived by the user. The chest piece 200 illustrated also has a conventional activation switch 244, which allows the user to readily activate or deactivate the stethoscope as desired. The activation switch 244 and the pressure switch 242 preferably act in coordination such that the chest piece is only activated when both switches (242, 244) are in their closed positions. The pressure switch 242 can interrupt power to one or more components of the stethoscope, or can interrupt transmission of the signal between components. Preferably, the pressure switch 242 interrupts transmission of the signals between the signal processing unit 24 and the earphones 14.

Figure 10:
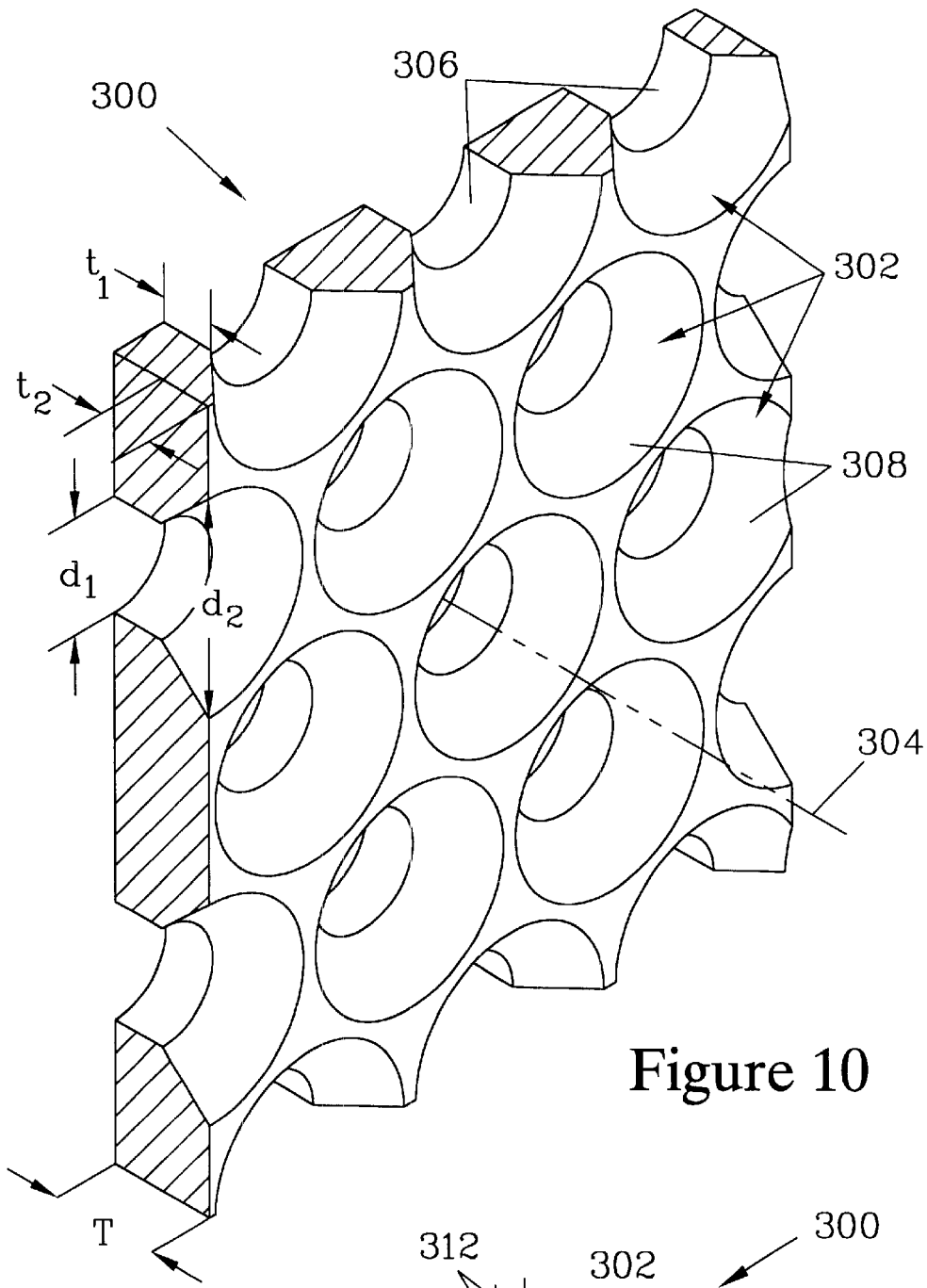
FIG. 10 is an isometric view showing a section of a preferred embodiment of the mechanical wave guide employed in the embodiment shown in FIG. 9.

FIG. 10 is an isometric view showing a section of a mechanical wave guide 300, illustrating a preferred configuration of this element of the present invention. The mechanical wave guide 300 is suitable for application where support of the membrane is not essential. This would be the situation in an application such as illustrated in FIG. 9. The mechanical wave guide 300 is preferably fabricated from a rigid material such as aluminum or a plastic such as polycarbonate, ABS, or similar semi-rigid or rigid plastic.

Figure 11:
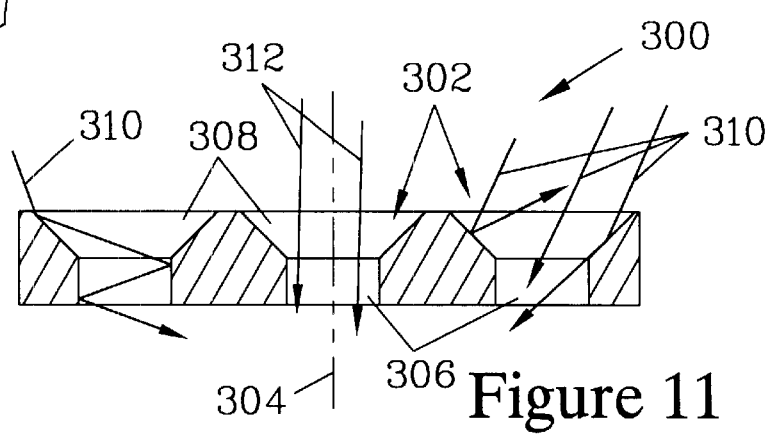
FIG. 11 is an end view of the section shown in FIG. 10.

The mechanical wave guide 300 has an array of sound passages 302 which are all parallel to an axis 304 which is substantially normal to the mechanical wave guide 300. In the mechanical wave guide 300, the sound passages 302 have both a cylindrical section 306 and a frustoconical section 308. The frustoconical section 308 is oriented towards a membrane (not shown) and is believed to enhance reflection of sound waves which are not parallel to the axis 304 away from the cylindrical section 306. As shown in the view of FIG. 11, sound waves arriving at the frustoconical section 308 an angle substantially inclined from the axis 304, as represented by rays 310, are mostly reflected at the angle of incidence away from the cylindrical section 306 or, if reflected into the cylindrical section 306, the inclination from the axis 304 is increased such that they are reflected further away from a focal point of a parabolic surface (not shown) placed behind the mechanical wave guide 300. However, sound waves arriving at the frustoconical section 308 an angle substantially parallel to the axis 304, as represented by rays 312, pass into the cylindrical section 306.

The mechanical wave guide 300 preferably has a thickness T of about 1/8 inch (3 mm). It is further preferred for the cylindrical section 306 of each of the sound passages 302 to have a depth $t_1$ of about 1/16 inch (1.5 mm) and a diameter d1 of about 1/8 inch (3 mm). It is preferred for the frustoconical section 308 of each of the sound passages 302 to have a depth $t_2$ of about 1/16 inch (1.5 mm) and a base diameter $d_2$ of about 1/4 inch (6 mm).

To maximize the intensity of sound passed through the mechanical wave guide 300, it is preferred for the sound passages 302 to be arranged in a hexagonal packed array to allow the greatest number of sound passages 302 for a given area of the mechanical wave guide 300.

Carrying the invention into Practice

Figure 12:
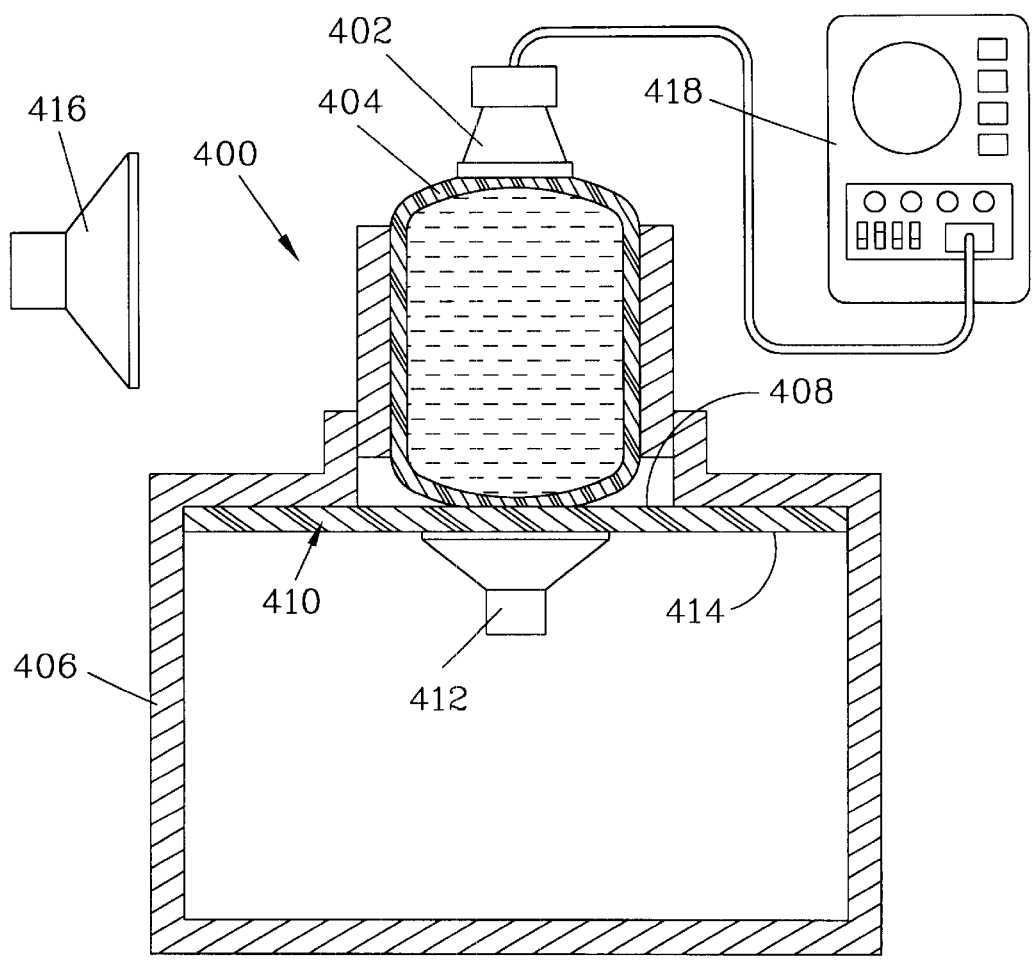
FIG. 12 is a schematic view of a testing apparatus employed to compare the performance of a chest piece of the present invention with a conventional stethoscope chest piece.

While to date a commercial stethoscope has not been fabricated employing the chest pieces of the present invention, one of the embodiments of the present invention (the embodiment shown in FIGS. 6–8) has been reduced to practice and its performance compared with a currently available commercial chest piece employed in a Littmann stethoscope. FIG. 12 is a schematic view of an artificial chest cavity test apparatus 400 which was employed to compare the performance of a the two chest pieces. The artificial chest cavity test apparatus 400 is employed to test a chest piece 402, and has a liquid-filled bladder 404 mounted to an enclosure 406. The bladder 404 is mounted on a top surface 408 of a sound panel 410, while a sound speaker 412 is mounted to a bottom surface 414 of the sound panel 410. The chest piece 402 being tested is placed against the bladder 404 in the same manner as it would be applied to the body of a patient. Sound signals are produced by the sound speaker 412, while noise signals are produced by a noise speaker 416 placed near the artificial chest cavity test apparatus 400. An oscilloscope 418, which the tests conducted was a Tektronix Model 2221 Digital Storage Oscilloscope, is employed to record and display the signals received by a transducer in the chest piece 402. The effectiveness of the present invention can be appreciated from comparing the results of embodiment against the performance of a conventional chest piece from a Littmann Master Classic model acoustic stethoscope, which had a microphone placed at the throat of the sound chamber.

The Littmann stethoscope was tested in an environment where the sound speaker 412 presented a simulated heartbeat consisting of three frequencies, approximately 62 Hz, 87 Hz, and 110 Hz, while the noise speaker 416 presented a recording of in-flight noise of a C-130 aircraft at a level of 85 dB. Under such conditions, the intensity of noise from the noise speaker 416 received through the chest piece 402 was significantly greater than the intensity of the simulated heartbeat presented by the sound speaker 412. The chest piece of the present invention was tested under the same conditions, and the intensity of the simulated heartbeat presented by the sound speaker 412 was the intensity of noise from the noise speaker 416 received by the chest piece 402.

Figure 13:
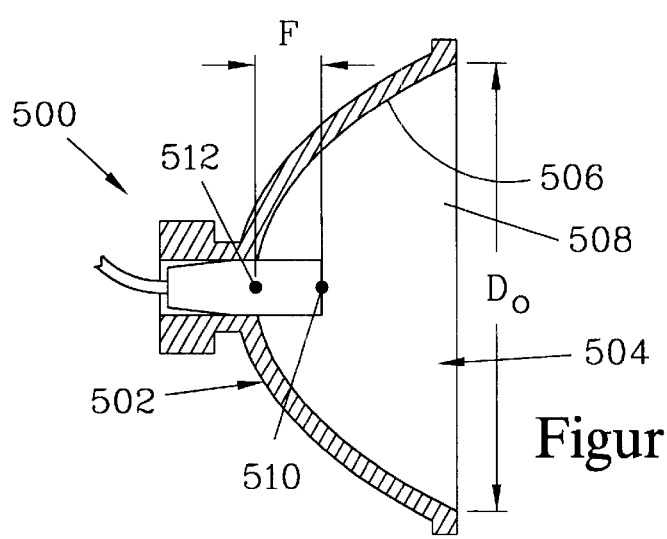
FIG. 13 is a schematic view of a chest piece of the present invention illustrating the preferred geometry of the paraboloid cavity surface.

FIG. 13 illustrates the dimensions of selected elements of a chest piece 500 of the present invention. The chest piece 500 again has a housing 502 with a cavity 504 bounded by a cavity surface 506 and terminating in a substantially planar opening 508. The cavity surface 506 bounds a paraboloid having a paraboloid focal point 510 and a paraboloid apex 512. The paraboloid shape of the cavity surface 506 is defined by a focal length F between the paraboloid apex 512 and the paraboloid focal point 510. The cavity 504 is also defined by an opening diameter $D_o$ at the substantially planar opening 508.

In one example, the paraboloid shape of the cavity surface 506 has the focal length F measure about 0.25 inches (6.4 mm) and the opening diameter $D_o$ measure about 1.66 inches (42.1 mm). In another example, the one used in the test discussed above, the paraboloid shape of the cavity surface 506 again has the focal length F measure about 0.25 inches (6.4 mm). In this example, the opening diameter $D_o$. measures about 1.25 inches (31.8 mm).

While the novel features of the present invention have been described in terms of particular embodiments and preferred applications, it should be appreciated by one skilled in the art that substitution of materials and modification of details obviously can be made without departing from the spirit of the invention.

What I claim is:

1. A chest piece suitable for use in a stethoscope and comprising:

a housing having a cavity which acts as a sound chamber, said cavity having a cavity surface which is a surface of revolution generated by rotating a parabola about its axis of symmetry to form a paraboloid having a paraboloid apex, a paraboloid focal point, and a paraboloid axis,
      said cavity terminating in said paraboloid apex and in a substantially planar opening, said opening being substantially normal to said paraboloid axis and positioned such that said paraboloid focal point resides in said cavity;

a transducer for converting received sounds into an electronic signal;

a bracket attached to said housing and configured so as to affix said transducer at or near said paraboloid focal point;

a membrane covering said opening so as to close said cavity, and a fluid which fills said cavity.

2. The chest piece of claim 1 wherein said cavity has a diameter of less than about 2 inches (51 mm).

3. The chest piece of claim 2 further comprising:
a bezel attaching to said housing and securing said membrane to said housing.

4. The chest piece of claim 2 wherein said bracket further comprises:
a rigid pedestal axially aligned with said paraboloid axis and passing through said paraboloid apex.

5. The chest piece of claim 2 wherein said bracket further comprises:
a spider bracket having rigid legs which attach to said cavity surface.

6. The chest piece of claim 4 wherein said fluid is a substantially incompressible liquid.

7. The chest piece of claim 5 wherein said fluid is a substantially incompressible liquid.

8. The chest piece of claim 4 wherein said fluid is processed to form a colloidal solution and forms a substantially incompressible gel.

9. The chest piece of claim 5 wherein said fluid is processed to form a colloidal solution and forms a substantially incompressible gel.

10. The chest piece of claim 5 wherein said paraboloid focal point is substantially displaced from said paraboloid apex and said spider bracket is in close proximity to said opening.

11. The chest piece of claim 4 wherein said housing has a pedestal passage through said paraboloid apex, further wherein said pedestal further comprises:
a transducer casing formed of a substantially resilient material, said transducer casing having a transducer recess configured to forcibly accept said transducer and having a lead passage configured to accept a lead wire connected to said transducer for conveying said electronic signal; and
a rigid mounting sleeve configured to forcibly accept said transducer casing and to mount into said pedestal passage in said housing,
thereby affixing said transducer with respect to said paraboloid focal point.

12. The chest piece of claim 11 further comprising:
a flange-engaging recess in said housing, said flange-engaging recess surrounding said pedestal passage;
a sealing flange formed on said transducer casing and extending from said rigid sleeve when said transducer casing is forcibly received therein, said sealing flange being configured to sealably engage said flange-engaging recess of said housing.

13. The chest piece of claim 12 further comprising:
a force ring configured to engage said sealing flange of said transducer casing; and
a cap nut which threadably engages said housing so as to compress said sealing flange between said flange-engaging recess and said force ring as said cap nut is tightened.

14. The chest piece of claim 10 wherein said spider bracket further comprises:
a central body in which said transducer is mounted, said central body being affixed to said rigid legs such that said transducer is directed toward said paraboloid apex of said housing,
further wherein the chest piece further comprises:
a supplemental transducer mounted to said central body of said spider bracket so as to be directed away from said paraboloid apex and toward said substantially planar opening of said housing.

15. The chest piece of claim 2 further comprising:
a pressure switch responsive to changes in fluid pressure in said cavity so as to interrupt said electronic signals from said transducer unless said membrane is pressed against a body with a force of at least about 2–4 oz (0.6–1.1 N).

16. An improved chest piece suitable for use in a stethoscope and having:
a housing having a cavity which acts as a sound chamber, the cavity terminating in a substantially planar opening,
a transducer for converting received sounds into an electronic signal,
a transducer support attached to the housing and configured so as to position the transducer within the cavity, the improvement comprising:
a mechanical wave guide for covering said substantially planar opening, said mechanical waveguide having a series of parallel sound passages therethrough.

17. The chest piece of claim 16 wherein said mechanical wave guide has a convex surface.

18. The chest piece of claim 17 further comprising;
a membrane which covers said convex surface of said mechanical wave guide so as to close the cavity.

19. The chest piece of claim 16 wherein each of said sound passages has a cylindrical section and a frustoconical section which is oriented toward the substantially planar opening of the housing, said sound passages being arranged in a hexagonal packed array.

20. The chest piece of claim 19 wherein said mechanical wave guide has a thickness T of about $\frac{1}{8}$ inch (3 mm), said cylindrical portion of each of said sound passages has a depth $t_1$ of about $\frac{1}{16}$ inch (1.5 mm) and a diameter $d_1$ of about $\frac{1}{8}$ inch (3 mm), and said frustoconical section of each of said sound passages has a depth $t_2$ of about $\frac{1}{16}$ inch (1.5 mm) and a base diameter $d_2$ of about $\frac{1}{4}$ inch (6 mm).

21. A chest piece suitable for use in a stethoscope and comprising:
a housing having a cavity which acts as a sound chamber, said cavity having a cavity surface which is a surface of revolution generated by rotating a parabola about its axis of symmetry to form a paraboloid having a paraboloid apex, a paraboloid focal point, and a paraboloid axis,
said cavity terminating in said paraboloid apex and in a substantially planar opening having a diameter of less than about 2 inches (51 mm), said opening being substantially normal to said paraboloid axis and positioned such that said paraboloid focal point resides in said cavity;
a transducer for converting received sounds into an electronic signal;
a transducer support attached to said housing and configured so as to position said transducer at or near said paraboloid focal point; and
a mechanical wave guide for covering said substantially planar opening, said mechanical wave guide having a series of sound passages therethrough, said sound passages extending parallel to said paraboloid axis of said housing.

22. The chest piece of claim 21 wherein said mechanical wave guide has a convex surface.

23. The chest piece of claim 22 further comprising:
a membrane which covers said convex surface of said mechanical wave guide so as to close said cavity.

24. The chest piece of claim 22 wherein said cavity is filled with a gel.

25. The chest piece of claim 21 wherein each of said sound passages has a cylindrical section and a frustoconical section which is oriented toward said substantially planar opening of said housing, said sound passages being arranged in a hexagonal packed array.

26. The chest piece of claim 25 wherein said mechanical wave guide has a thickness T of about ⅛ inch (3 mm), said cylindrical portion of each of said sound passages has a depth $t_1$ of about 1/16 inch (1.5 mm) and a diameter $d_1$ of about ⅛ inch (3 mm), and said frustoconical section of each of said sound passages has a depth $t_2$ of about 1/16 inch (1.5 mm) and a base diameter $d_2$ of about ¼ inch (6 mm).

27. A chest piece suitable for use in a stethoscope and comprising:

a housing having a cavity which acts as a sound chamber, said cavity terminating in a substantially planar opening;

a primary transducer for converting received sounds into an electronic signal;

a transducer support attached to said housing and configured so as to position said transducer within said cavity such that said transducer is directed away from said substantially planar opening of said housing; and a supplemental transducer mounted to said transducer support so as to be directed toward said substantially planar opening of said housing.

* * * * *